(12) United States Patent
Murray et al.

(10) Patent No.: US 7,358,411 B2
(45) Date of Patent: Apr. 15, 2008

(54) HYDROCRACKING OF DIPHENYLALKANES

(75) Inventors: Brendan Dermot Murray, Houston, TX (US); Garo Garbis Vaporciyan, Houston, TX (US)

(73) Assignee: Shell Oil Company, Houston, TX (US)

( * ) Notice: Subject to any disclaimer, the term of this patent is extended or adjusted under 35 U.S.C. 154(b) by 716 days.

(21) Appl. No.: 10/872,703

(22) Filed: Jun. 21, 2004

(65) Prior Publication Data

US 2005/0049446 A1 Mar. 3, 2005

Related U.S. Application Data

(60) Provisional application No. 60/483,756, filed on Jun. 30, 2003.

(51) Int. Cl.
*C07C 4/26* (2006.01)

(52) U.S. Cl. .................. 585/476; 585/485; 585/484

(58) Field of Classification Search ............... 585/476, 585/485, 484
See application file for complete search history.

(56) References Cited

U.S. PATENT DOCUMENTS

| | | | |
|---|---|---|---|
| 4,232,177 A | 11/1980 | Smith, Jr. | 585/324 |
| 4,242,530 A | 12/1980 | Smith, Jr. | 585/510 |
| 4,443,559 A | 4/1984 | Smith, Jr. | 502/527 |
| 4,822,936 A | 4/1989 | Maurer et al. | 585/259 |
| 5,266,546 A | 11/1993 | Hearn | 502/300 |
| 5,348,710 A | 9/1994 | Johnson et al. | 422/211 |
| 5,475,159 A | 12/1995 | Singleton et al. | |
| 5,905,178 A | 5/1999 | Hildreth | 585/258 |
| 6,455,712 B1 | 9/2002 | Vaporciyan et al. | |

FOREIGN PATENT DOCUMENTS

| | | |
|---|---|---|
| GB | 786668 | 11/1957 |
| GB | 1122702 | 1/1966 |
| WO | 01/70714 | 9/2001 |
| WO | WI92947126 | 6/2002 |
| WO | WO02048125 | 6/2002 |
| WO | WO02048127 | 6/2002 |
| WO | 02/072507 | 9/2002 |

OTHER PUBLICATIONS

International Search Report, dated Jan. 13, 2005.
2001607516 Derwent Abstract 2001.
2001590165 Derwent Abstract 2001.
2001590164 Derwent Abstract 2001.
2001590161 Derwent Abstract 2001.
200159501 Derwent Abstract 2001.

*Primary Examiner*—Thuan Dinh Dang

(57) ABSTRACT

The invention relates to a hydrocracking process involving the steps of reacting a diphenyl alkane having a formulation of R1R2C(Ph)-(C)n(H)m-C(Ph)R3R4 with hydrogen using a catalyst containing a metal selected from the group consisting of Group IB and Group VIII metal compounds, preferably on an acidic support, to produce alkylbenzene(s) having a structure of R1R2C(Ph)R5 and R6(Ph)CR3R4; wherein the total number of carbon atoms for R5 and R6 is equal to n; wherein R1, R2, R3, R4 each is a H or a hydrocarbon group having 1-10 carbon atoms.

19 Claims, No Drawings

HYDROCRACKING OF DIPHENYLALKANES

This application claims the benefit of U.S. Provisional Application No. 60/483,756 filed Jun. 30, 2003, the entire disclosure of which is hereby incorporated by reference.

FIELD OF THE INVENTION

The present invention relates to catalytic hydrocracking of a diphenylalkane to produce alkylbenzene. The present invention further relates to a process for catalytic hydrocracking of 2-methyl-2,4-diphenylpentane to produce isopropyl benzene ("cumene").

BACKGROUND OF THE INVENTION

Substantial quantities of diphenylalkanes are produced as a byproduct in various chemical processes involving the reaction or the production of (substituted) benzene-containing compounds such as styrene, phenol, dialkyl benzene and cumene. For example, 2-methyl-2,4-diphenylpentane and dimethyl-2,3-diphenylbutane are produced as byproducts in many processes which use cumene, such as in the cumene-phenol peroxidation process, and in the process for the recovery of cumene from cumyl alcohol.

WO01/70714, assigned to Sumitomo, describes a process relating to oxidizing isopropylbenzene (also known as "cumene") to obtain isopropylbenzene peroxide as an oxygen carrier for the epoxidation of propylene to produce propylene oxide and isopropylbenzene alcohol (cumyl alcohol). The isopropylaryl alcohol is dehydrated/hydrogenated, via a hydrogenolysis step, to isopropylbenzene (cumene) and recycled for repeated use. During the hydrogenolysis step, substantial quantities of cumene dimer are produced as undesirable by-products due to the further hydrogenation or dimerization of cumene, which remains in the hydrogenation bed after it is produced, but before exiting.

U.S. Pat. No. 6,455,712, assigned to Shell, describes a process for producing alkylene oxide (also known as oxirane) compounds, such as propylene oxide, by oxidizing olefin with alkylbenzene hydroperoxide obtained by oxidizing alkylbenzene with oxygen. The alkylbenzene hydroperoxide is converted to alkylaryl alcohol which is dehydrated/hydrogenated via a multi-step process of hydrogenolysis, followed by fractionation, to separate alkylbenzene from other side product for reuse for making alkylbenzene. Substantial quantities of alkylaryl alcohol could be converted to dimers/oligomers of alkylbenzene as side products.

WO02/072507, assigned to Sumitomo, describes a process for hydrocracking 2,3-dimethyl-2,3-diphenylbutane in the presence of a copper chromium catalyst. The conversion rate at 220° C. is only about 84%. Moreover, there are usually other cumene dimers, such as 2-methyl-2,4-diphenylpentane, produced as side-products in processes involving cumene which are not mentioned in this patent.

It is therefore desirable to develop an efficient process which would recover undesirable alkylbenzene dimer or oligomer by-products produced and convert them into higher value alkylbenzene with high yield at relatively low temperature and low costs, so that alkylbenzene may be cost effectively recycled for repeated use in the same commercial process or for other industrial use.

SUMMARY OF THE INVENTION

The present invention relates to a process for hydrocracking of a diphenyl alkane to produce an alkylbenzene with a high conversion rate at a mild temperature, which process comprises the steps of:

reacting a diphenyl alkane having a formulation of R1R2C(Ph)-(C)n(H)m-C(Ph)R3R4 with hydrogen using a catalyst comprising a metal selected from the group consisting of Group IB and Group VIII metal compounds, preferably on an acidic support, to produce alkylbenzene(s) having a structure of R1R2C(Ph)R5 and R6(Ph) CR3R4;

wherein the total number of carbon atoms for R5 and R6 is equal to n;

wherein R1, R2, R3, R4 each is a H or a hydrocarbon group having 1-10 carbon atoms.

Particular examples of diphenyl alkane include 2-methyl-2,4-diphenylpentane and 3-dimethyl-2,3-diphenyl butane.

DETAILED DESCRIPTION OF INVENTION

The present invention relates to a process for catalytic hydrocracking of a diphenyl alkane to produce an alkylbenzene. Illustrative and non-limiting examples of suitable hydrogenation or hydrocracking catalysts include catalysts comprising Group VIII metal or Group IB metal, particularly those comprising copper, palladium, platinum and nickel.

As a particular embodiment of the present invention, the catalyst employed is supported by an acidic carrier (also known as "support"), particularly a carrier which is in an "acidic hydrogen form". The term of "acidic hydrogen form" means that 50% or more of ion exchangeable cations are protons (also known as "$H^+$" or "hydrogen (+) ions"). Not intended to be bound by the theory, it is proposed that acidic hydrogens help promote the hydrocracking reaction and increase the acidity of the catalyst. The highly active catalyst is able to hydrocrack the diphenylalkane under relatively mild conditions, thereby minimizing the production of side products, such as alkyl cyclohexanes, and lower the utility costs. Non-limiting illustrative examples of an acidic support include silica, silica-alumina, and zeolite, such as Mordenite, Na/H-Mordenite, H-Mordenite, beta-zeolite, H-beta-zeolite, Y-zeolite, H-Y-zeolite, and the like. When zeolites are used, it is preferred that they are in the acidic hydrogen form.

In one particular embodiment of the present invention, the catalysts contain from about 0.1% to about 5% wt., particularly from about 0.2% to 2% wt, calculated as the weight of the metal on the basis of the total weight of the catalyst, of Group VIII metal or a Group VIII metal compound as principal catalytic component, alone or with promoters and modifiers such as palladium/gold, palladium/silver, cobalt/zirconium, nickel, preferably deposited on an acidic support, more preferably deposited on an acidic support in acidic hydrogen form. One illustrative example of a suitable catalytic material comprises palladium oxide or palladium, particularly about 0.1% to 5.0% by weight, and more particularly 0.2% to 2% by weight, calculated as the weight of the metal on the basis of the total weight of the catalyst, supported on an appropriate support medium such as zeolite (particularly Mordenite or H-Mordenite) or silica. A preferred catalyst comprises from about 0.2% to about 2% by weight of palladium on H-Mordenite.

As other particular embodiments of the present invention, Group IB metals of the Periodic Table of Elements, such as copper, are used as the principle catalytic component, alone or with promoters and modifiers such as chromium, zinc, zirconium, aluminum, magnesium, a rare earth metal, Group VIII metals, etc. for hydrogenation. The Group IB metal-containing catalysts preferably contain from about 10% to about 80%, particularly from about 30% to about 75%, more particularly from about 50% to about 70%, as the weight of the oxide basis the total weight of the catalyst, of a Group IB metal, particularly on an acidic support, more particularly on a support in acidic hydrogen form. Specific non-limiting examples of such catalysts include catalysts comprising copper, Raney copper, copper/chrome, copper/zinc, copper/zinc/chrome, copper/zinc/zirconium, copper/silica, copper/alumina and other copper-based catalyst systems, particularly those supported by an acidic support, more particularly those supported by a support in an acidic hydrogen form. Some specific illustrative examples include commercially available copper on silica catalyst, T-366 (having approximately 54 wt. % of copper on silica as a press extrudate or formed extrudate), obtainable from Sud Chemie; copper chromite catalyst, G-22/2, obtainable from Sud Chemie; and Cu/Zn/Zr catalyst prepared according Example 3 of U.S. Pat. No. 5,475,159 herein incorporated by reference; and the like. Combinations of these catalysts may also be used. Such catalysts were found to give good results at relatively low temperature. In one non-limiting illustrative embodiment of the present invention, these catalysts are preferably used at a temperature of from 100° C. to 250° C. Such catalysts may comprise from 5 percent by weight to 80 percent by weight, calculated as the oxide, basis the total weight of the catalyst, of copper. Further, such catalysts may contain from 10 percent by weight to 80 percent by weight, calculated as the oxide, basis the total weight of the catalyst, of zinc, from 15 percent to 85 percent by weight of acidic carrier, particularly a support in acidic hydrogen form. A particular example of the catalyst contains from about 10 percent by weight to about 80 percent by weight, calculated as the oxide, basis the total weight of the catalyst, of copper, from about 10 percent by weight to about 80 percent by weight, calculated as the oxide, basis the total weight of the catalyst, of zinc, from about 0.1 percent by weight to about 20 percent by weight, calculated as the oxide, basis the total weight of the catalyst, of rare earth and from about 10% to about 80 weight percent of acidic carrier, particularly a support in acidic hydrogen form. A further particular catalyst contains from about 10 percent by weight to about 80 percent by weight, calculated as the oxide, basis the total weight of the catalyst, of copper, from about 10 percent by weight to about 80 percent by weight, calculated as the oxide, basis the total weight of the catalyst, of zinc, and from about 0.05 percent by weight to about 30 percent by weight, basis the total weight of the catalyst, of aluminum. A further particular catalyst contains from about 10 percent by weight to about 80 percent by weight, calculated as the oxide, basis the total weight of the catalyst, of copper, from about 10 percent by weight to about 80 percent by weight, calculated as the oxide, basis the total weight of the catalyst, of zinc, from about 0.05 percent by weight to about 30 percent by weight, basis the total weight of the catalyst, of zirconium, and about 10 weight percent to 80 weight percent of acidic carrier, particularly a support in acidic hydrogen form. Another preferred catalyst contains from about 10 percent by weight to about 80 percent by weight, calculated as the oxide, basis the total weight of the catalyst, of copper, from about 10 percent by weight to about 80 percent by weight, calculated as the oxide, basis the total weight of the catalyst, of zinc, from about 0.05 percent by weight to about 30 percent by weight, basis the total weight of the catalyst, of zirconium, and from about 0.05 percent by weight to about 30 percent by weight, basis the total weight of the catalyst, of aluminum, and about 10 weight percent to 80 weight percent of acidic carrier, particularly a support in acidic hydrogen form. And a further preferred catalyst contains from about 10 percent by weight to about 80 percent by weight, calculated as the oxide, basis the total weight of the catalyst, of copper, from about 10 percent by weight to about 80 percent by weight, calculated as the oxide, basis the total weight of the catalyst, of zinc, from about 0.05 percent by weight to about 30 percent by weight, basis the total weight of the catalyst, of magnesium, from about 0.1 percent by weight to about 20 percent by weight, calculated as the oxide, basis the total weight of the catalyst, of rare earth, and and about 10 weight percent to 80 weight percent of acidic carrier, particularly a support in acidic hydrogen form.

As a particular embodiment of the present invention, the afore-mentioned hydrocracking catalysts are reduced by hydrogen prior to being loaded in the reactor. As a non-limiting illustrative example, a hydrocracking catalyst is crushed and sized into appropriate size, e.g. 6-20 mesh, particles. The catalyst is introduced into a reactor and slowly reduced by heating the catalyst particles to a temperature of e.g. about 150-250° C. at a rate of from about 1° C. to about 10° C., particularly from about 1.5° C. to about 5° C. per minute, while flowing about 0.001° C. to about 0.1° C., specifically about 0.02° C. to 0.10 wt. % hydrogen in nitrogen at a rate of 1-200, specifically 2-30 L/Hr. The catalyst is allowed to reduce at 150-250° C. for 1-10 hours and then the hydrogen content in the nitrogen is doubled every 1-5 hours until the gas is 1-10%, specifically 2-5 wt. % hydrogen in nitrogen. Catalysts containing copper are preferably reduced at a temperature of between 150-200° C. to minimize sintering. The catalyst is reduced for a final one to five hour period and then cooled while maintaining gas flow. After cooling, the reactor is capped without allowing any air to enter and the gas flow is stopped. The reactor is opened in a nitrogen filled environment and the catalyst removed.

The particles of reduced catalyst, prepared by the afore-mentioned procedure are loaded onto a reactor over bed supports, e.g. made of porous plate/tray or screen, optionally in a nitrogen filled environment. The reduced catalysts are sized and shaped to stay above the bed supports.

Without limiting the scope of the present invention, the diphenylalkane has a formulation of R1R2C(Ph)-(C)n(H)m-C(Ph)R3R4 and the alkylbenzene produced has a structure of R1R2C(Ph)R5 and R6(Ph)CR3R4; wherein the total number of carbon atoms for R5 and R6 is equal to n; n is from 0 to 10, preferably from 0 to 5; wherein R1, R2, R3, R4 each is hydrogen or a hydrocarbon group having 1-10 carbon atoms. The number of hydrogens is equal to or less than 2n, depending on the degree of branching in (C)n(H)m.

As one particular embodiment of the present invention, the diphenylalkane is 2-methyl-2,4-diphenylpentane. Another particular embodiment comprises a mixture of 2-methyl-2,4-diphenylpentane and dimethyl-2,3-diphenylbutane.

As other particular embodiments of the present invention, additional alkyl groups may be present on the aromatic rings of the diphenylalkane, and the alkylbenzene produced comprises an alkylbenzene selected from the group consisting of para-di(iso-propyl)benzene, meta-di(iso-propyl)benzene, ortho-di(iso-propyl)benzene, 1-ethyl-4-(iso-propyl)benzene, 1-ethyl-3-(iso-propyl)benzene, 1-ethyl-4-(iso-propyl) benzene and mixtures thereof.

The pressure for the hydrocracking reaction should range between from about 0 psig to about 400 psig, particularly from about 5 psig to 300 psig, and more particularly from about 0 psig to about 140 psig (or about 1-10 bar). The temperature of the hydrocracking reactor is from about 140° C. to about 300° C., particularly from about 160° C. to about 280° C., more particularly from about 180° C. to about 235° C.

The hydrogenation flow rate must be adjusted such that it is sufficient to support the hydrocracking reaction and replace hydrogen lost from the catalyst. At least a stoichiometric amount of hydrogen relative to the alkenylbenzene dimers must be present in the system to be available for the reaction. As a non-limiting example, a small excess of hydrogen flow is provided to occlude the hydrogen into the liquid and to accommodate the nature of the reaction between a gas and a liquid.

The feed weight hourly space velocity (WHSV), may vary over a very wide range within the other condition parameters, and may be from about 0.1 to about 100, from about 0.2 to about 20 particularly from about 0.5 to about 15 liters per hour. WHSV, as used herein, means the unit weight of feed per hour entering the reaction distillation reactor per unit weight of catalyst in the reactor catalyst bed.

The percent conversion of the dimers of alkylbenzene to alkylbenzene, as used herein, is defined as the following:
% conversion of dimers=(wt. % of dimers in feed−wt. % of dimers in product)×100 Wt. % of dimers in feed As a particular embodiment of the present invention, from about 86.0% to about 100.0% by weight, particularly from about 90.0% to about 100.0% by weight, more particularly from about 94.0% to about 100%, still more particularly from about 97.5% to about 100.0%, and still more particularly from about 98.0% to about 100.0% by weight of the dimers of alkylbenzene in the hydrocracking reaction media may be converted to compounds with only one benzene ring at a temperature of from about 185° C. to about 235° C. The same ranges of cracking also may be accomplished at from about 140° C. to about 300° C., particularly from about 160° C. to about 280° C. As an illustrative particular embodiment, from about 97.5 to about 100.0 percent by weight of dimers of alkylbenzene is converted to compounds with (only) one benzene ring at a temperature from about 185° C. to about 235° C. As another illustrative particular embodiment, from about 97.5% to about 100.0%, more particularly from about 98.0% to about 100.0 percent by weight of dimers of alkylbenzene is converted to compounds with (only) one benzene ring at a temperature from about 185° C. to about 225° C.

As a particular embodiment of the present invention, from about 86.0% to about 100.0% by weight, particularly from 90.0% to about 100.0%, more particularly from about 94.0% to about 100.0%, still more particularly from about 97.5% to about 100.0% and still more particular from about 98.0% to about 100.0% by weight of the 2-methyl-2,4-di(3-isopropylphenyl)pentane may be converted to compounds with only one benzene ring such as isopropylbenzene at a temperature of from about 180° C. to about 235° C. As another particular embodiment of the present invention, from about 86.0% to about 100.0% by weight, particularly from 90.0% to about 100.0%, more particularly from about 94.0% to about 100%, still more particularly from about 97.5% to about 100%, and still more particular from about 98.0% to about 100.0% by weight of the the 2-methyl-2,4-di(3-isopropylphenyl)pentane may be converted to isopropylbenzene at a temperature of from about 185° C. to about 235° C. The same ranges of cracking also may be accomplished at from about 140° C. to about 300° C., particularly from about 160° C. to about 280° C. As an illustrative particular embodiment, from about 97.5% to about 100.0 percent by weight of 2-methyl-2,4-di (3-isopropylphenyl)pentane is converted to cumene at a temperature of from about 185° C. to about 235° C. As another illustrative particular embodiment, from about 97.5% by weight, and more particularly from about 98.0% to about 100.0 percent by weight of 2-methyl-2,4-di(3-isopropylphenyl)pentane is converted to cumene at a temperature of from about 185° C. to about 225° C.

As a particular embodiment of the present invention, from about 86.0% to about 100% by weight, particularly from 90.0% to about 100.0%, more particularly from about 94.0% to about 100.0%, still more particularly from about 97.5% to about 100%, and still more particularly from about 98.0% to about 100.0% by weight of the mixture of 2-methyl-2,4-di (3-isopropylphenyl)pentane and 2,3-dimethyl-2,3-diphenylbutane may be converted to compounds with only one benzene ring at a temperature of from about 180° C. to about 235° C. The same ranges of cracking also may be accomplished at from about 140° C. to about 300° C., particularly from about 160° C. to about 280° C. As an illustrative particular embodiment, from about 97.5% to about 100.0 percent by weight of mixtures of 2-methyl-2,4-di(3-isopropylphenyl)pentane and 2,3-dimethyl-2,3-diphenylbutane is converted to cumene at a temperature from about 185° C. to about 235° C. As another illustrative particular embodiment, from about 97.5% to about 100.0%, and more particularly from about 98.0% to about 100.0 percent by weight of a mixture of 2-methyl-2,4-di(3-isopropylphenyl)pentane and 2,3-dimethyl-2,3-diphenylbutane is converted to cumene at a temperature of from about 185° C. to about 225° C.

The feed steam may come from a fixed bed reactor (recovered after fractional distillation), from the bottom stream of a catalytic distillation reactor of a alkylphenylalcohol hydrogenation reaction, optionally fractionated to remove lighter weight alkylphenylalcohol etc., or from a cumene-phenol peroxidation process. These streams are optionally diluted with alkylbenzene prior to being fed to the hydrocracking reactor to moderate the heat generated in the hydrocracking reaction, thereby improving the control of the reaction in the hydrocracker.

As an illustrative example, the feed stream contains from about 0.1% to about 100%, particularly from about 0.1% to about 10%, and more particularly from about 0.2% to about 2% by weight of diphenylalkane; from about 0% to about 99%, particularly from about 25% to about 95%, and more particularly from about 60% to about 90% by weight of alkylbenzene; from about 0% to about 20%, particularly from about 0% to about 5%, and more particularly from about 0% to about 1% by weight of alkenylbenzene; and from about 0% to about 25%, particularly from about 0% to about 10%, and more particularly from about 0% to about 5% by weight of alkylphenyl alcohol. As a specific illustrative example of a particular embodiment of the present invention, the feed stream contains from about 0.1% to about 100%, particularly from about 0.1% to about 1%, and more particularly from about 0.2% to about 2% by weight of 2,3-dimethy-2,3-diphenyl butane and/or 2-methyl-2,4-diphenyl pentane; from about 0% to about 99%, particularly from about 25% to about 95%, and more particularly from about 60% to about 90% by weight of cumene; from about 0% to about 20%, particularly from about 0% to about 5%, and more particularly from about 0% to about 1% by weight of alpha-methyl styrene; from about 0% to about 5 weight percent of ethyl benzene; from about 0% to about 5 weight percent of di-, tri-isopropyl benzene, ethyl benzene, propylbenzene, ethyl-isopropyl benzene, etc., or mixtures thereof; and from about 0% to about 25%, particularly from about 0% to about 10%, and more particularly from about 0% to about 5% by weight of cumyl alcohol.

The invention will be illustrated by the following illustrative embodiments which are provided for illustration purpose only and are not intended to limit the scope of the instant invention.

ILLUSTRATIVE EMBODIMENTS

I. Illustrative Embodiment I

I(A) Preparation of Hydrocracking Catalyst Pd-Mordenite Catalyst

A mixture of 1500 grams of sodium mordenite, (having the following properties: a surface area of 430 square meters per gram; an average crystallite size of around 1 micron; a cyclohexane adsorption uptake of 7.6 cc/g; and a molar silica to alumina ratio of 11.1), 9000 grams of ammonium nitrate and 15 liters of 1.5 M nitric acid was heated to 50° C. and stirred for five hours. The solid material was filtered off and washed with 25 liters of deionized water. This treatment of the Mordenite with ammonium nitrate in nitric acid was repeated twice with fresh ammonium nitrate and nitric acid each time. After each treatment, the solid material was filtered off and washed with water and dried overnight at 120° C. Palladium was added to the zeolite to a level of 0.35 percent by weight by treatment with an aqueous solution containing tetraamine palladium nitrate and an excess of ammonium nitrate prepared by dissolving 6.55 grams of tetramine palladium nitrate in 308 grams of deionized water and adding to this solution 4.92 grams of ammonium nitrate. The palladium solution was then co-mulled with 1083 grams of dealuminated mordenite having an LOI (loss of igination at 750° C. for 2 hours) of 10.6%. The palladium-containing mordenite was uniformly mixed and then 338 grams of pseudoboehmite alumina (Catapal B which is commercially available from Vista Chemical Company) having an LOI of 28.4% was added and allowed to mix. The mixture was extruded and the 1.6 mm extrudates were dried in air for 16 hours at 125° C., and then calcined in flowing air at 500° C. for two hours. The catalyst was crushed and sized to 6-20 mesh particles and then reduced using the procedure as described in IIA below.

IB. Hydrocracking of Cumene Dimer Using Pd on H-Mordenite Catalyst

The bottom stream from a catalytic distillation column, for the catalytic distillation of cumyl alcohol to produce cumene, was distilled to yield a cumene dimer rich mixture that was diluted with cumene and fed into a fixed bed hydrogenation reactor loaded with the acidic palladium on H-Mordenite catalyst as described in I(A) for hydrocracking under the condition as provided in TABLE 1 below. The results are shown in TABLE 2 below.

TABLE 1

| Feedrate | 33.5 g/hr |
|---|---|
| Reaction Temperature | 220° C. |
| Pressure | 10 bar |
| Hydrogen Flowrate | 4 L/Hr |
| Catalyst Weight | 33.5 g (before reduction) |

TABLE 2

Fixed Bed Cumene Dimers To Cumene Results With Palladium on H-Mordenite Catalyst at 220° C.

| Component | Cumene dimers in cumene (FEED) | Fixed Bed Product |
|---|---|---|
| 2,3-Dimethyl-2,3-diphenylbutane, (wt %) | 1.94 | 0.06 |
| 2-methyl-2,4-diphenylpentane, (wt %) | 1.03 | 0.02 |
| Cumene, (wt %) | 96.75 | 99.82 |
| Isopropylcyclohexane, (wt %) | 0.08 | 0.08 |
| Alpha-Methyl styrene, (wt %) | 0.20 | 0.02 |

II. Illustrative Embodiment II

IIA Preparation of Hydrocracking Catalyst T-366 Catalyst

A commercially available copper on silica catalyst, T-366, available from Sud Chemie, having 54 wt. % of Cu on silica extruded into 3.2 mm extrudate, is further processed using the following procedure for the catalytic cracking experiments.

Five grams of Sud Chemie T-366 copper on silica catalyst (3 mm tablets) was crushed and sized into 6-20 mesh particles. The catalyst was mixed with 45 grams of 80 mesh silicon carbide and centered inside a 69 cm long stainless steel reactor tube between beds of 20 mesh SiC and glass wool. The reactor tube had an internal diameter of 1.5 cm. The catalyst was slowly reduced by heating the catalyst particles at a rate of 3° C. per minute from 20° C. to 180° C. while flowing 0.05 wt. % hydrogen in nitrogen at a rate of 10 L/Hr. The catalyst was allowed to reduce at 180° C. for 2 hours and then the hydrogen content in the nitrogen was doubled every 2 hours until the gas was 3.2 wt. % hydrogen in nitrogen. The catalyst was reduced for a final two-hour period and then cooled while maintaining gas flow. After cooling, the reactor was capped without allowing any air to enter and the gas flow was stopped. The reactor was opened in a nitrogen filled glove box and the catalyst and silicon carbide were separated by screen sieve.

Cumene Dimers Using T-366 Copper on Silica Catalyst

The bottom stream from a catalytic distillation column, for the catalytic distillation of cumyl alcohol to produce cumene, was distilled to yield a cumene dimer rich mixture that was diluted with cumene and fed into a fixed bed hydrogenation loaded with the T-366 catalyst as described in II(A) for hydrocracking under the condition as provided in TABLE 3 below. The results are shown in TABLE 4 below.

TABLE 3

| Feedrate | 33.5 g/hr |
|---|---|
| Reaction Temperature | 260° C. |
| Pressure | 10 bar |
| Hydrogen Flowrate | 4 L/Hr |
| Catalyst Weight | 33.5 g (before reduction) |

TABLE 4

Fixed Bed Cumene Dimer To Cumene Results
With T-366 Catalyst At 260° C.

| Component | Cumene dimers in cumene (FEED) | Fixed Bed Product |
|---|---|---|
| 2,3-Dimethyl-2,3-diphenylbutane, (wt %) | 1.94 | 0.05 |
| 2-methyl-2,4-diphenylpentane, (wt %) | 1.03 | 0.09 |
| Cumene, (wt %) | 96.75 | 99.54 |
| Isopropylcyclohexane, (wt %) | 0.08 | 0.18 |
| α-methyl styrene, (wt %) | 0.20 | 0.09 |

III. Comparative Example

IIIA. Preparation of Hydrogenation Catalyst Palladium on Carbon

Pressed granules of 0.5 wt. % of palladium on carbon, available from the Calsicat division of Mallinckrodt Incorporated was mixed with silicon carbide and reduced according the same procedure as described in IIA above.

IIIB. Hydrocracking of Cumene Dimers with Palladium on Carbon Catalyst

The bottom stream from a catalytic distillation column, for the catalytic distillation of cumyl alcohol to produce cumene, was distilled to yield a cumene dimer rich mixture that was diluted with cumene and fed into a fixed bed hydrogenation loaded with the acidic palladium on carbon catalyst as described in III(A) for hydrocracking under the condition as provided in TABLE 5 below. The results are shown in TABLE 6 below.

TABLE 5

| Feedrate | 33.5 g/hr |
|---|---|
| Reaction Temperature | 220° C. |
| Pressure | 10 bar |
| Hydrogen Flowrate | 4 L/Hr |
| Catalyst Weight | 33.5 g (before reduction) |

TABLE 6

Fixed Bed Cumene Dimers To Cumene Results
With Palladium on Carbon Catalyst at 220° C.

| Component | Cumene dimers in cumene (FEED) | Fixed Bed Product |
|---|---|---|
| 2,3-Dimethyl-2,3-diphenylbutane, (wt %) | 1.94 | 0.10 |
| 2-methyl-2,4-diphenylpentane, (wt %) | 1.03 | 0.10 |
| Cumene, (wt %) | 96.75 | 99.60 |
| Isopropylcyclohexane, (wt %) | 0.08 | 0.16 |
| α-methyl styrene, (wt %) | 0.20 | 0.04 |

IV. Conclusion

As shown in Illustrative Embodiment IB, when a catalyst of Pd loaded on a highly acidic support is used for hydrocracking cumene dimers (2,3-dimethyl-2,3-diphenybutane and 2-methyl-2,4-diphenylpentane) to cumene, the conversion rate at 220° C. C is about 98.0% and the selectivity to cumene is close to 100%. As shown in Illustrative Embodiment IIB, when a catalyst of Cu loaded on silica (an acidic support) is used for hydrocracking of cumene dimers (2,3-dimethyl-2,3-diphenybutane and 2-methyl-2,4-diphenylpentane) to cumene, the conversion rate is about 95.3%, and the selectivity is about 100%.

In contrast, as shown in Comparative Example IIIB, when a non acidic catalyst of 0.5 wt. % Pd loaded on a carbon support is used for hydrocracking of cumene dimers (2,3-dimethyl-2,3-diphenybutane and 2-methyl-2,4-diphenylpentane) to cumene, the conversion rate is 93.3%, and the selectivity is about 100%.

In view of the foregoing, Pd on a highly acidic support (H-Mordenite) provides a higher hydrocracking conversion rate, compared to the same loaded on a non-acidic support.

The ranges and limitations provided in the instant specification and claims are those which are believed to particularly point out and distinctly claim the instant invention. It is, however, understood that other ranges and limitations that perform substantially the same function in substantially the same manner to obtain the same or substantially the same result are intended to be within the scope of the instant invention as defined by the instant specification and claims.

We claim:

1. A hydrocracking process comprising the steps of:
reacting a diphenyl alkane having a formulation of R1R2C(Ph)-(C)n(H)m-C(Ph)R3R4 with hydrogen using a catalyst comprising a metal selected from the group consisting of Group IB and Group VIII metal compounds on an acidic support to produce alkylbenzene(s) having a structure of R1R2C(Ph)R5 and R6(Ph)CR3R4;
wherein the total number of carbon atoms for R5 and R6 is equal to n; and,
wherein R1, R2, R3, R4 each is a hydrogen or a hydrocarbon group having 1-10 carbon atoms.

2. The process of claim 1 wherein the diphenyl alkane comprises 2-methyl-2,4-di(3-isopropylphenyl)-pentane, 2,3-dimethyl-2,3-di(3-isopropyl-phenyl)butane or a mixture thereof.

3. The process as described in claim 2, wherein said support in an acidic hydrogen form is selected from the group consisting of silica, silica-alumina zeolites, and mixtures thereof.

4. The process as described in claim 1, wherein from about 86.0% to about 100.0% by weight of the diphenyl alkane is converted to isopropylbenzene at a temperature from about 140° C. to about 300° C.

5. The process as described in claim 4, wherein said catalyst support is selected from the group consisting of zeolites, silica, silica-alumina and mixtures thereof.

6. The process as described in claim 4, wherein the catalyst comprises from about 0.01 to about 5% by weight of Group IB catalyst on an acidic support.

7. The process as claimed in claim 4, wherein said catalyst comprises a copper metal compound.

8. The process as claimed in claim 4, wherein said catalyst is palladium on Mordenite.

9. The process as claimed in claim 1, wherein said alkylbenzene produced comprises an alkylbenzene selected from the group consisting of para-di(iso-propyl)benzene, meta-di(iso-propyl)benzene, rortho-di(iso-propyl)benzene, 1-ethyl-4-(iso-propyl)benzene, 1-ethyl-3-(iso-propyl)benzene, 1-ethyl-4-(iso-propyl)-benzene.

10. The process as claimed in claim 1, wherein from about 90.0 to about 100.0% by weight of diphenylalkane is converted to alkylbenzene at a temperature from about 160° C. to about 280° C.

11. A hydrocracking process comprising the steps of reacting a mixture comprising 2-methyl-2,4-di(3-isopropylphenyl)pentane and 2,3-dimethyl-2,3-di(3-isopropylphenyl) butane with a catalyst comprising Group VIII metal or Group IB metal on an acidic support at a temperature from about 140° C. to about 300° C., wherein from about 86.0% to about 100.0% by weight of the combined weight of 2-methyl-2,4-di(3-isopropylphenyl)-pentane,3-dimethyl-2,3-di(3-isopropylphenyl) butane is converted to isopropylbenzene.

12. The process as claimed in claim 11, wherein the acidic support is selected from the group consisting of zeolites, silica, silica-alumina and mixtures thereof.

13. The process as claimed in claim 11, wherein said catalyst comprises a copper metal compound.

14. The process as claimed in claim 11, wherein said catalyst is palladium on Mordenite.

15. A hydrocracking process comprising reacting 2-methyl-2,4-di(3-isopropylphenyl)pentane with a catalyst comprising palladium on a support in an acidic hydrogen form to produce isopropylbenzene.

16. The process as described in claim 15, wherein from about 90.0% to about 100.0% of the 2-methyl-2,4-di(3-isopropylphenyl)pentane is converted to isopropylbenzene at a temperature from about 160° C. to about 280° C.

17. A hydrocracking process comprising reacting 2-methyl-2,4-di(3-isopropylphenyl)pentane with a catalyst comprising palladium on an acidic support to produce isopropylbenzene.

18. A hydrocracking process comprising reacting 2-methyl-2,4-di(3-isopropylphenyl)pentane with a catalyst comprising Group VIII metal or Group IB metal on a support in an acidic hydrogen form at a temperature from about 140° C. to about 300° C., wherein from about 86.0% to about 100.0% of the 2-methyl-2,4-di(3-isopropylphenyl)-pentane is converted to compounds with only one benzene ring.

19. A hydrocracking process comprising the steps of reacting a mixture comprising 2-methyl-2,4-di(3-isopropylphenyl)pentane and 2,3-dimethyl-2,3-di(3-isopropylphenyl)butane with a catalyst comprising palladium on H-Mordenite to produce isopropylbenzene.

* * * * *